US010188963B2

(12) United States Patent
Byström et al.

(10) Patent No.: US 10,188,963 B2
(45) Date of Patent: Jan. 29, 2019

(54) REACTOR FOR BIOLOGICAL OR CHEMICAL TRANSFORMATION

(71) Applicant: SPINCHEM AB, Umeå (SE)

(72) Inventors: Emil Byström, Umeå (SE); Henrik Scherman, Umeå (SE); Knut Irgum, Bullmark (SE)

(73) Assignee: SPINCHEM AB, Umea (SE)

( * ) Notice: Subject to any disclaimer, the term of this patent is extended or adjusted under 35 U.S.C. 154(b) by 318 days.

(21) Appl. No.: 15/027,758

(22) PCT Filed: Sep. 26, 2014

(86) PCT No.: PCT/SE2014/051118
§ 371 (c)(1),
(2) Date: Apr. 7, 2016

(87) PCT Pub. No.: WO2015/060764
PCT Pub. Date: Apr. 30, 2015

(65) Prior Publication Data
US 2016/0243462 A1      Aug. 25, 2016

(30) Foreign Application Priority Data
Oct. 25, 2013   (SE) .................................. 1351272-8

(51) Int. Cl.
*B01J 8/10*   (2006.01)
*B01J 19/18*  (2006.01)
(Continued)

(52) U.S. Cl.
CPC .............. *B01D 15/18* (2013.01); *B01F 7/163* (2013.01); *B01F 7/1645* (2013.01);
(Continued)

(58) Field of Classification Search
CPC ...................... B01J 8/10; B01J 19/1875; B01J 2208/00938; B01J 2208/028;
(Continued)

(56) References Cited

U.S. PATENT DOCUMENTS 2,658,642 A  *  11/1953  Casella ............... A47J 43/1025
                                                   248/318
4,172,877 A     10/1979  Schwaig
(Continued)

FOREIGN PATENT DOCUMENTS

FR       2850039 A1     7/2004
JP       S5970734 U     5/1984
(Continued)

OTHER PUBLICATIONS

International Search Report dated Nov. 11, 2014 for PCT Application No. PCT/SE2014/051118.
(Continued)

*Primary Examiner* — Jennifer A Leung
(74) *Attorney, Agent, or Firm* — Moser Taboada

(57) ABSTRACT

The present invention relates to a new reactor for performing, by means of at least one solid reaction member, biological or chemical transformation, or physical or chemical trapping from, or release of agents to, a fluidic medium, which reactor is comprised of a reactor vessel comprising means for enhancing fluidic shear stress, and a transformation device operatively mounted in said reactor vessel. The invention also provides a kit of parts comprising a reactor vessel comprising means for enhancing fluidic shear stress and a transformation device. Finally, the invention provides a method of using said reactor and/or said kit of parts for biological or chemical transformation or physical or chemical trapping from, or release of agents to, a fluidic medium, by means of at least one solid reaction member.

9 Claims, 12 Drawing Sheets

Figure 1:
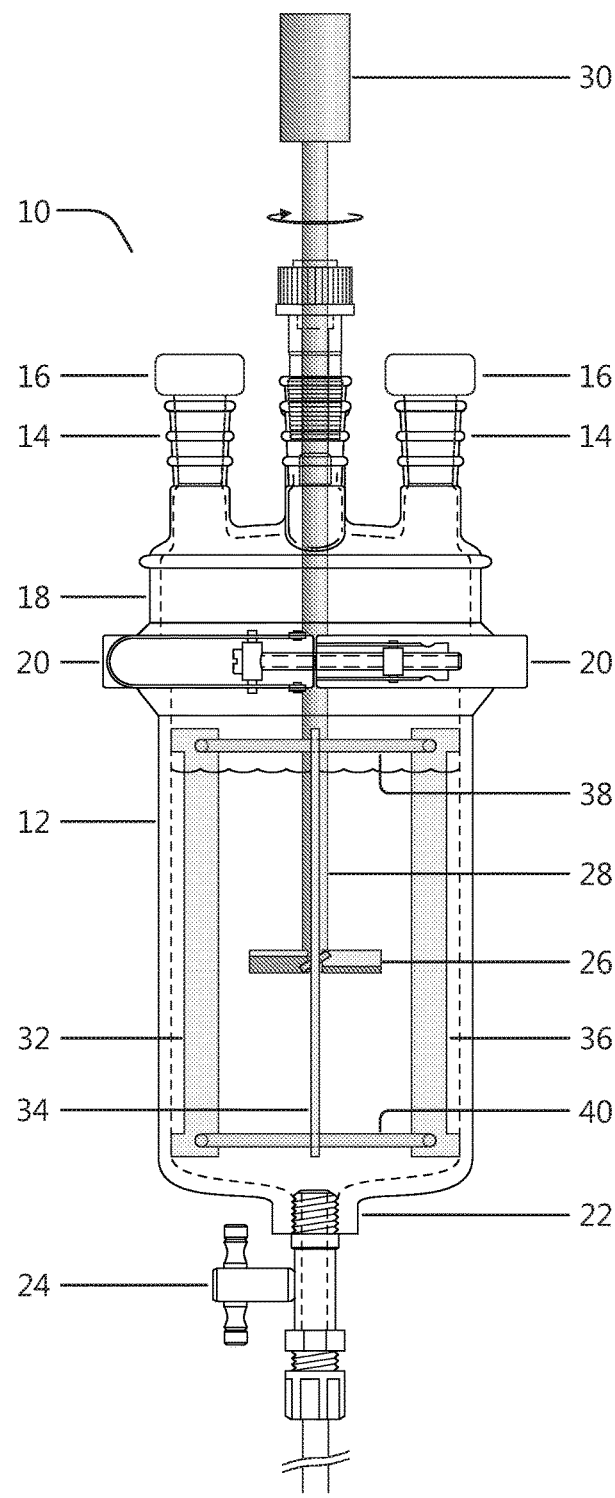

(51) Int. Cl.
| | |
|---|---|
| B01D 15/18 | (2006.01) |
| C12M 1/06 | (2006.01) |
| C12M 1/00 | (2006.01) |
| B01F 7/16 | (2006.01) |
| B01F 15/00 | (2006.01) |
| B01J 20/20 | (2006.01) |
| B01J 19/00 | (2006.01) |

(52) U.S. Cl.
CPC .......... *B01F 15/00896* (2013.01); *B01J 8/10* (2013.01); *B01J 19/006* (2013.01); *B01J 19/0066* (2013.01); *B01J 19/18* (2013.01); *B01J 19/1875* (2013.01); *B01J 20/20* (2013.01); *C12M 27/02* (2013.01); *C12M 27/20* (2013.01); *B01F 2215/0427* (2013.01); *B01F 2215/0431* (2013.01); *B01J 2208/028* (2013.01); *B01J 2219/00768* (2013.01)

(58) Field of Classification Search
CPC .. B01J 2208/00876; B01J 2219/00768; C12M 1/02; C12M 1/10; C12M 1/16; C12M 27/20; C12M 27/22; C12M 27/24
See application file for complete search history.

(56) References Cited

U.S. PATENT DOCUMENTS

| | | | |
|---|---|---|---|
| 4,683,062 A | | 7/1987 | Krovak et al. |
| 2002/0110508 A1 | | 8/2002 | Campo et al. |

FOREIGN PATENT DOCUMENTS

| | | | | |
|---|---|---|---|---|
| JP | 02203780 A | * | 8/1990 | ............ C12M 27/14 |
| JP | H02-203780 A | | 8/1990 | |
| JP | H04-354531 A | | 8/1992 | |
| WO | WO-0249751 A1 | | 6/2002 | |
| WO | WO-2008137846 A2 | | 11/2008 | |
| WO | WO-2011098570 A2 | | 8/2011 | |
| WO | WO-2015050491 A1 | | 4/2015 | |

OTHER PUBLICATIONS

Mallin et al., "Efficient Biocatalysis with Immobilized Enzymes or Encapsulated Whole Cell Microorganism by Using the SpinChem Reactor System", CHEMCATCHEM, vol. 5, Issue 12, pp. 3529-3532, Oct. 11, 2013.

Extended European Search Report dated May 31, 2017 for Application No. 14855257.3.

Office Action dated Sep. 18, 2018 for Application No. 2016-525947.

* cited by examiner

Prior art

REACTOR FOR BIOLOGICAL OR CHEMICAL TRANSFORMATION

FIELD OF INVENTION

The present invention relates to a new reactor for performing, by means of at least one solid reaction member, biological or chemical transformation, or physical or chemical trapping from, or release of agents to, a fluidic medium, which reactor is comprised of a reactor vessel having a specific internal design, and a transformation device operatively mounted in said reactor vessel. The invention also provides a kit of parts comprising a reactor vessel having said specific internal design and a transformation device. Finally, the invention provides a method of using said reactor and/or said kit of parts for biological or chemical transformation or physical or chemical trapping from, or release of agents to, a fluidic medium, by means of at least one solid reaction member.

BACKGROUND OF THE INVENTION

Heterogeneous processes in chemistry and biotechnology are unit operations that encompass a solid member (including, but not limited to, immobilized chemical reagents, catalysts, scavengers, reaction supports, trapping sorbents, or immobilized biological materials such as enzymes, or cells or fragments thereof) contacting a fluidic medium carrying reactants or other agents, sample solutes, and/or products of the interactive processing of fluid-conveyed agent(s) with the solid member(s). Most such heterogeneous processes are critically dependent on convective flow of the fluidic medium to establish the necessary mass transfer between the fluidic and solid phases. As a consequence, solid/fluid heterogeneous systems are therefore often operated in a continuous flow through mode, in which case a conventional packed column with a suitable design is often the preferred format for encapsulating the solid member that is to be transited or percolated by the reaction medium. Numerous processes are, however, unfit for continuous processing. This applies in particular to processes where the solid member is a soft and compressible gel which is prone to collapse in a packed column bed, in transformation schemes where sequential addition of agents and/or removal of by-products or desired products are necessary, or where the physical or chemical conditions must otherwise be altered during the course of processing with the solid member. In those cases, a batch-wise processing model is often preferred. Such batch-wise heterogeneous processing can either be done by suspending the solid member directly in the fluid medium as particulate material under agitation, a process that will normally call for a filtration or sedimentation step to separate the phases after the process has been brought to an end. Alternatively, the fluidic medium can be circulated from the batch reactor through a packed reservoir containing the solid member by means of a specially designed flow system comprising pumps and/or valves or the like, in order to accomplish the convective mass transfer needed for the transformation to take place. Such reactors are often quite complicated and must regularly be built on-site and adapted for a specific purpose.

The challenge of establishing efficient convective mass transfer between solid and fluid phases has been addressed in different ways. Some interesting alternatives are disclosed in WO 2011/098570, which relates to devices for performing biological or chemical transformation, or physical or chemical trapping from, or release of agents to, a fluidic medium by means of a solid reaction member. These devices are comprised of a flow distributor having a fluid medium inlet, a fluid medium outlet, at least one confinement where said transformation, trapping, or release of agents is performed, and a means for rotating, rocking, wagging, or oscillating the flow distributor, by which action fluidic medium in which it is submerged is pumped through a bed of solid member contained within the flow distributor.

As a result of this pumping action, use of the devices disclosed in WO 2011/098570 leads to increased convective mass transfer, and accordingly improved performance of most heterogeneous transformation schemes. One of the reasons for these enhanced convective mass transfer properties is the ability of the flow distributor to use a combination of centrifugal force and flow dynamics to draw fluid through the central inlet(s) and discharge it through the peripheral outlets, resulting in a pumping action that predominantly draws fluid from the larger central inlet located at the bottom of the device. However, there is still a need for devices capable of providing even more increased convective mass transfer and an increased ratio between solid reagent and fluidic reaction medium, in order to improve the performance of biological and chemical transformation, physical and chemical trapping and release of agents by means of a solid reaction member even further. Factors that hamper the efficient use of flow distributor devices disclosed in WO 2011/098570 in a cylindrical reactor are the formation of solid body rotation and plughole vortices, accompanied by suction of gases, which can be difficult to get rid of, into the flow distributor. The conventional way of solving the problem of solid body rotation and vortex formation for standard impeller-stirred batch reactors (FIG. 1) is to disturb the rotational flow in the reactor by furnishing the vessel with a set of baffles 10 (H. A. Jakobsen, "Chemical reactor modeling: Multiphase reactive flows", Springer Verlag: Berlin/Heidelberg, 2008; pp. 679-684), which are normally implemented as several (typically four) vertical flow-interrupting elements that are placed at some distance from the inner wall of the reactor in order to avoid the formation of unstirred fluid pockets. However, as is evident from FIG. 1, the inclusion of a conventional set of baffles results in a substantial increase in the total fluid volume of the reactor. Such excess volume is often detrimental to the kinetics of the intended transformations, since it will prevent the use of a high volume ratio between the solid reaction member and the fluidic phase. For an equal charged amount of reactants in the fluid phase, the concentration will thereby become lower, which has a negative effect on reaction kinetics in most cases. Conventional baffles are furthermore impractical to implement in small scale laboratory reactors.

SUMMARY OF THE INVENTION

It has now turned out to be possible to produce a reactor which leads to substantial increase in the convective mass transfer of heterogeneous transformation schemes, while at the same time improving the reaction kinetics by reducing the volume of the fluidic medium, in comparison with prior art, and accordingly further improve the performance of biological and chemical transformations, and physical and chemical trapping from or, release of agents to, the fluidic media being processed by such schemes.

In a first aspect, the invention provides a reactor for performing, by means of at least one solid reaction member(s), biological or chemical transformation, or physical or chemical trapping from, or release of agents to, a fluidic media, said reactor comprising a cylindrical reactor vessel having a first end part, a second end part, and an inner wall between these parts, in which reactor vessel a transformation device has been mounted, said transformation device comprising a flow distributor having an essentially cylindrical shape, a first essentially flat surface, a second essentially flat surface, and a peripheral wall having an essentially circular cross-section, at least one fluid medium inlet adapted for receiving fluid medium, and optionally adapted for receiving initially suspended solid reaction member(s), located in vicinity of the centre of said first and/or second surface, at least one fluid medium outlet permeable for said fluid medium but impermeable for solid reaction members, said outlet(s) being located on said peripheral wall, a driving shaft located on said first surface for enabling rotation or oscillation of the flow distributor, and at least one confinement wherein said solid members can be trapped and said transformation is performed; and a means for rotating and/or oscillating the device;

wherein said inner wall of the reactor vessel comprises means for enhancing the fluidic shear stress in any of the two rotary directions along said inner wall between said first end part and said second end part.

In a second aspect, the invention provides a kit for performing a biological or chemical transformation, or physical or chemical trapping from, or release of agents to, a fluidic media by means of a solid reaction member, comprising:

a) a cylindrical reactor vessel having a first end part, a second end part and an inner wall between these parts, wherein said inner wall comprises means for enhancing the fluidic shear stress in any of the two rotary directions along said inner wall between said first end part and said second end part; and b) a flow distributor having an essentially cylindrical shape, a first essentially flat surface, a second essentially flat surface, and a peripheral wall having an essentially circular cross-section, at least one fluid medium inlet adapted for receiving fluid medium and optionally adapted for receiving initially suspended solid members located at the centre of said first and/or second surface, at least one fluid medium outlet permeable for said fluid medium but impermeable for solid members, said outlet being located on said peripheral wall, a driving shaft located on said first surface for enabling rotation or oscillation of the flow distributor, and at least one confinement wherein said solid members can be trapped and said transformation is performed.

In a third aspect, the invention provides a method of using a reactor according to the first aspect for performing a biological or chemical transformation, or physical or chemical trapping from, or release of agents to, in a fluidic media by means of a solid reaction member.

BRIEF DESCRIPTION OF THE ENCLOSED FIGURES

Figure 2:
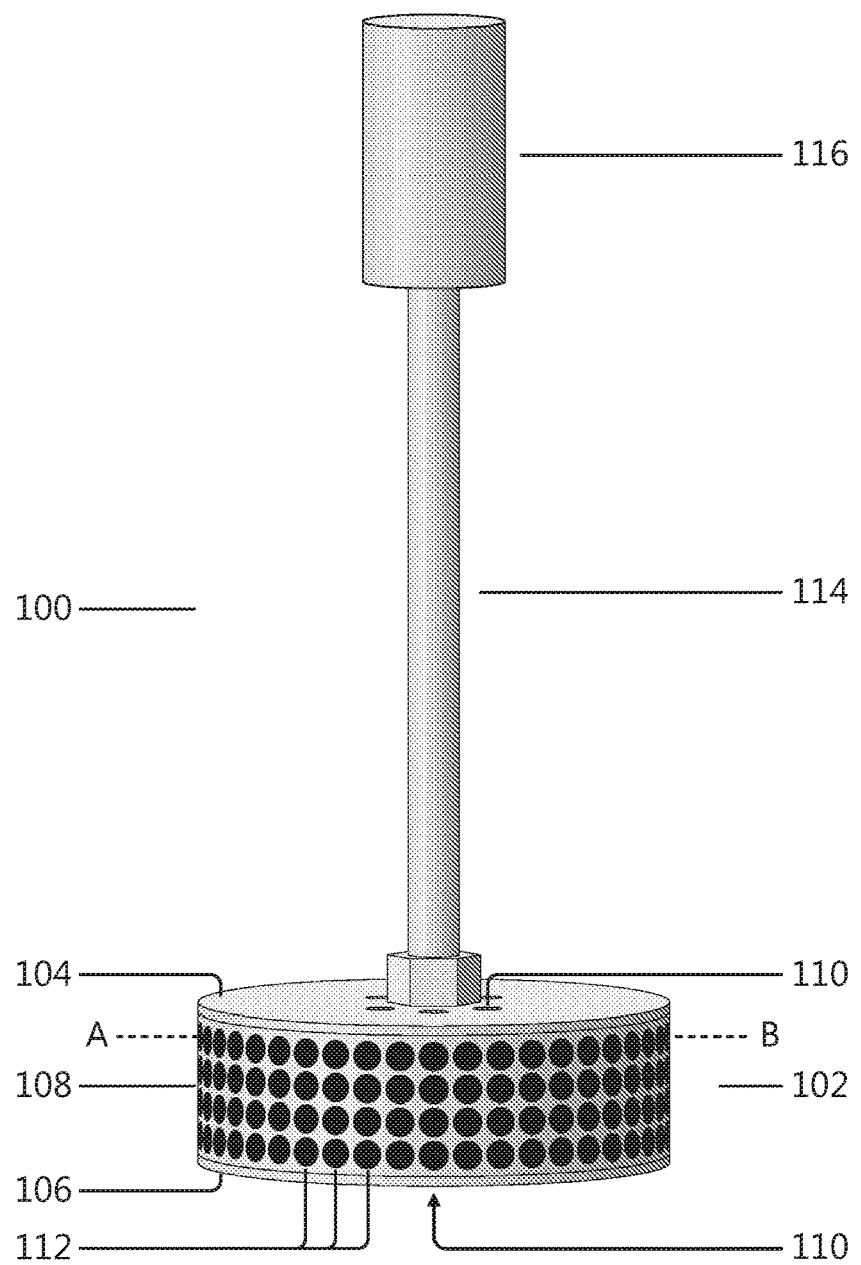

The present invention will now be further disclosed with reference to the enclosed figures, in which:

FIG. 1 presents a side view of a conventional reaction set-up for performing a biological or chemical transformation, or physical or chemical trapping from, or release of agents to, a fluidic media by means of a solid reaction member;

FIG. 2 shows a side view of an embodiment of a transformation device

Figure 3:
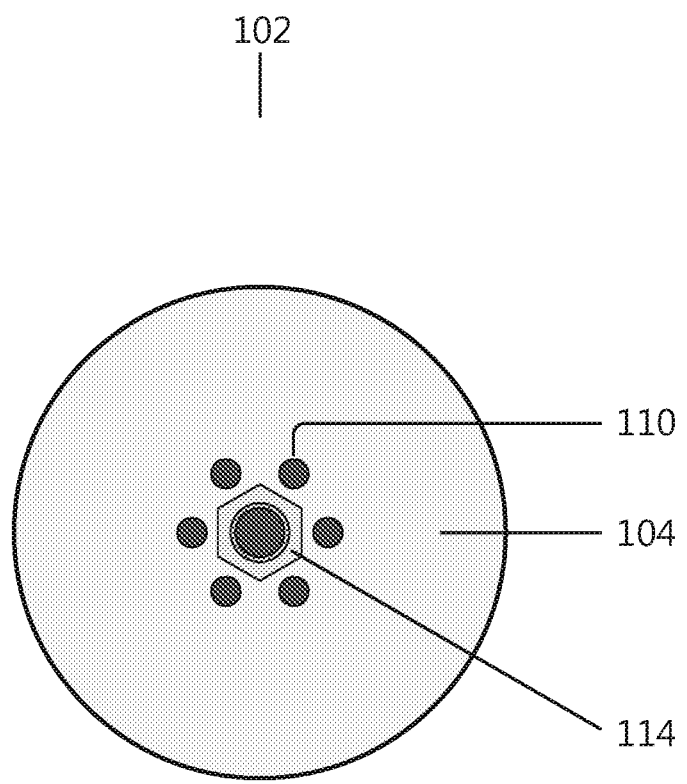
Figure 4:
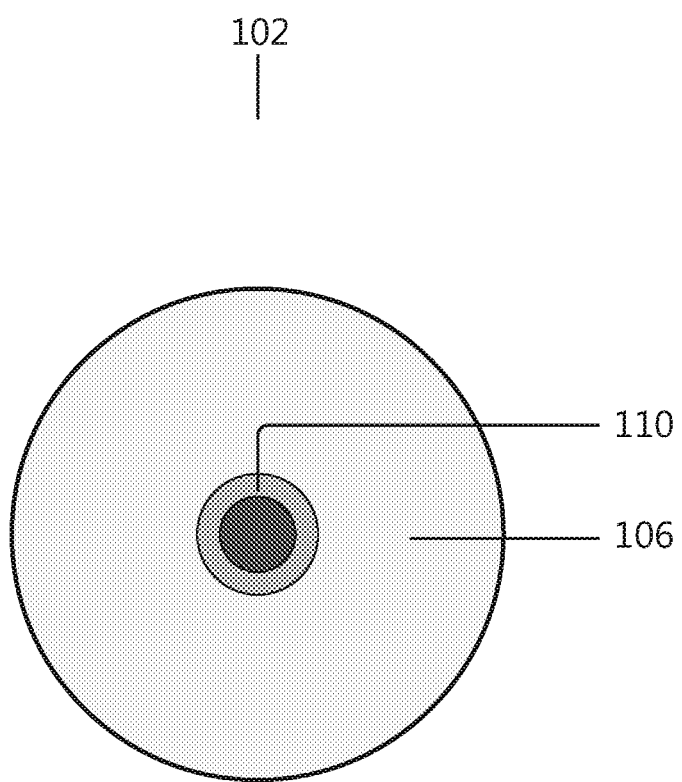
Figure 5:
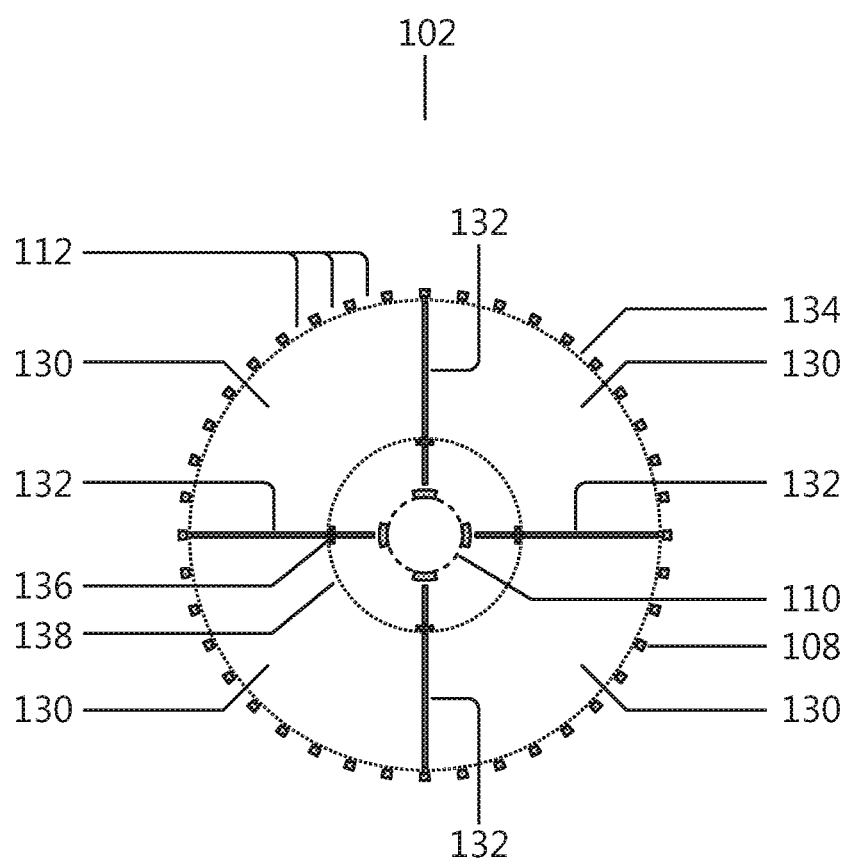

FIG. 3 outlines the second surface of an embodiment of the flow distributor;

FIG. 4 discloses a view of the first surface of an embodiment of the flow distributor of the transformation device in FIG. 2;

FIG. 5 shows a horizontal cross-sectional view from below along the line A-B of the embodiment of a transformation device shown in FIG. 2.

Figure 6:
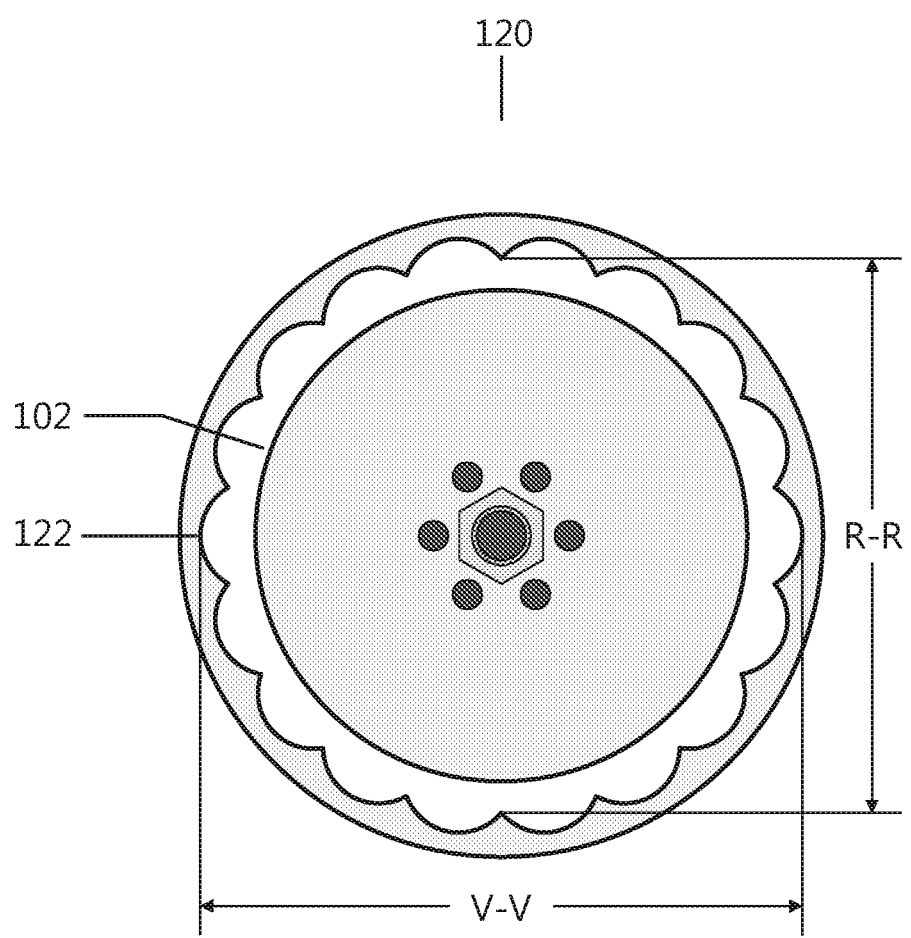
Figure 7:
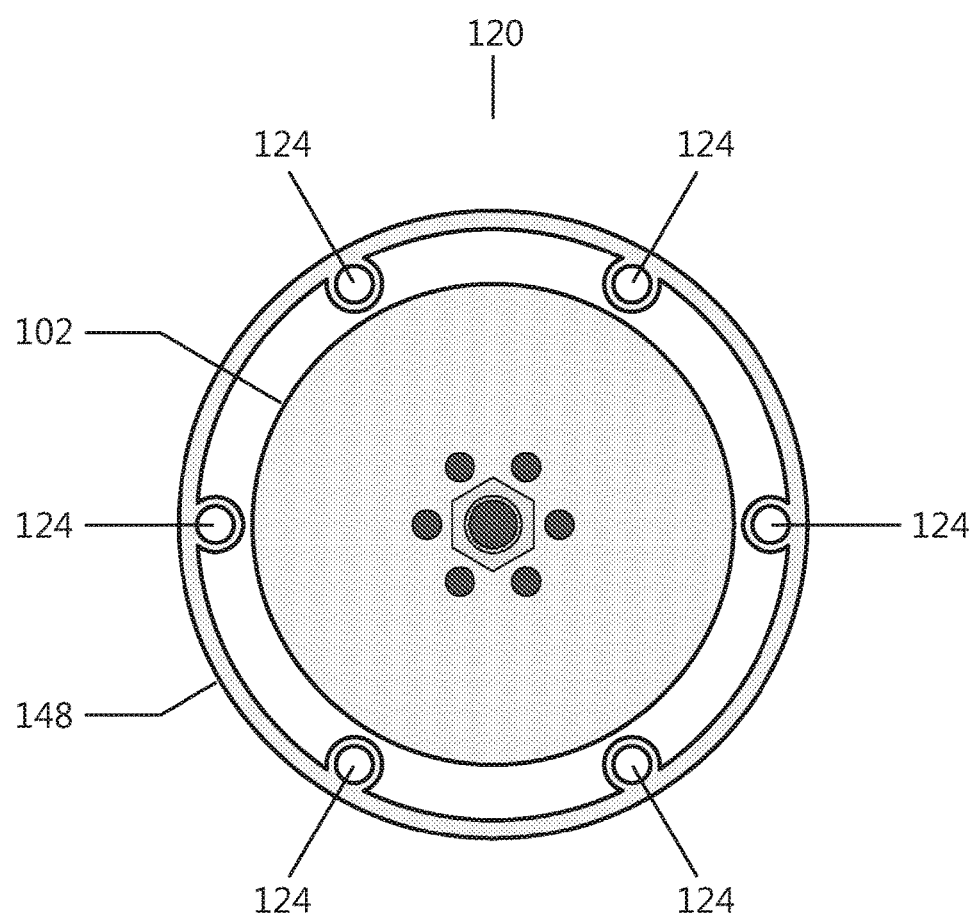
Figure 8:
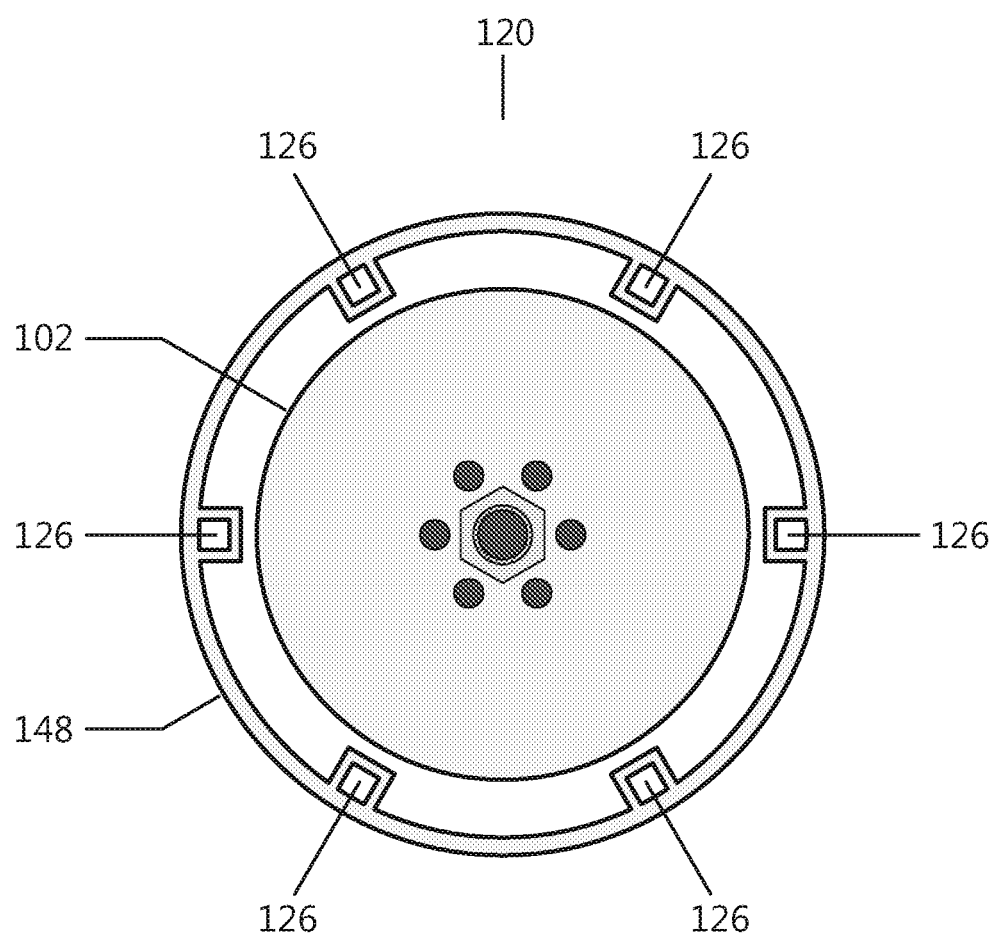
Figure 9:
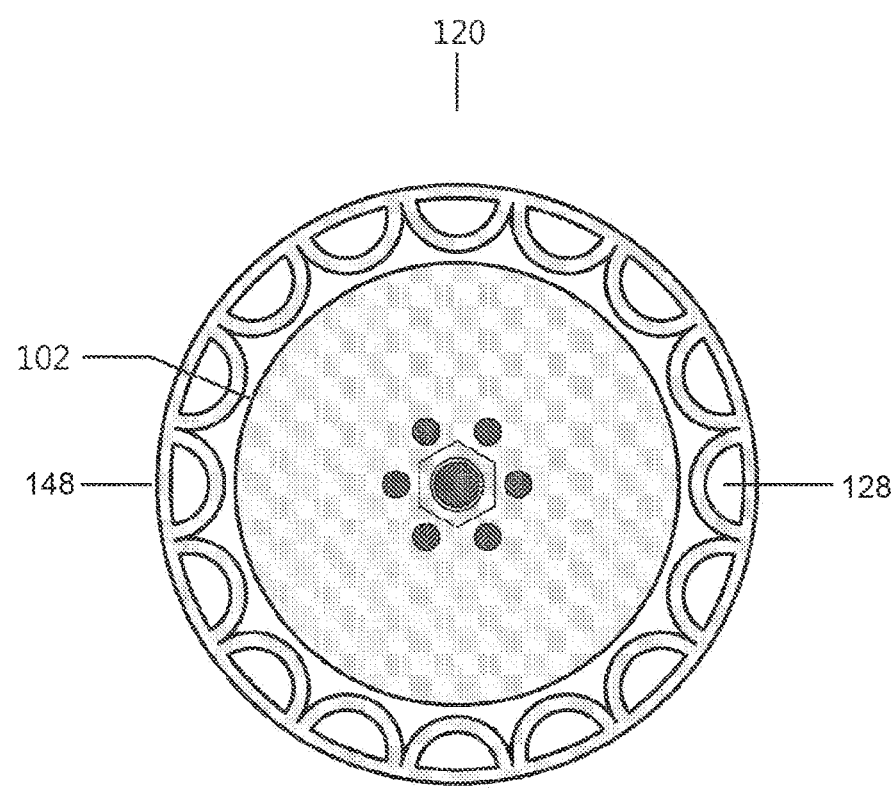
Figure 10:
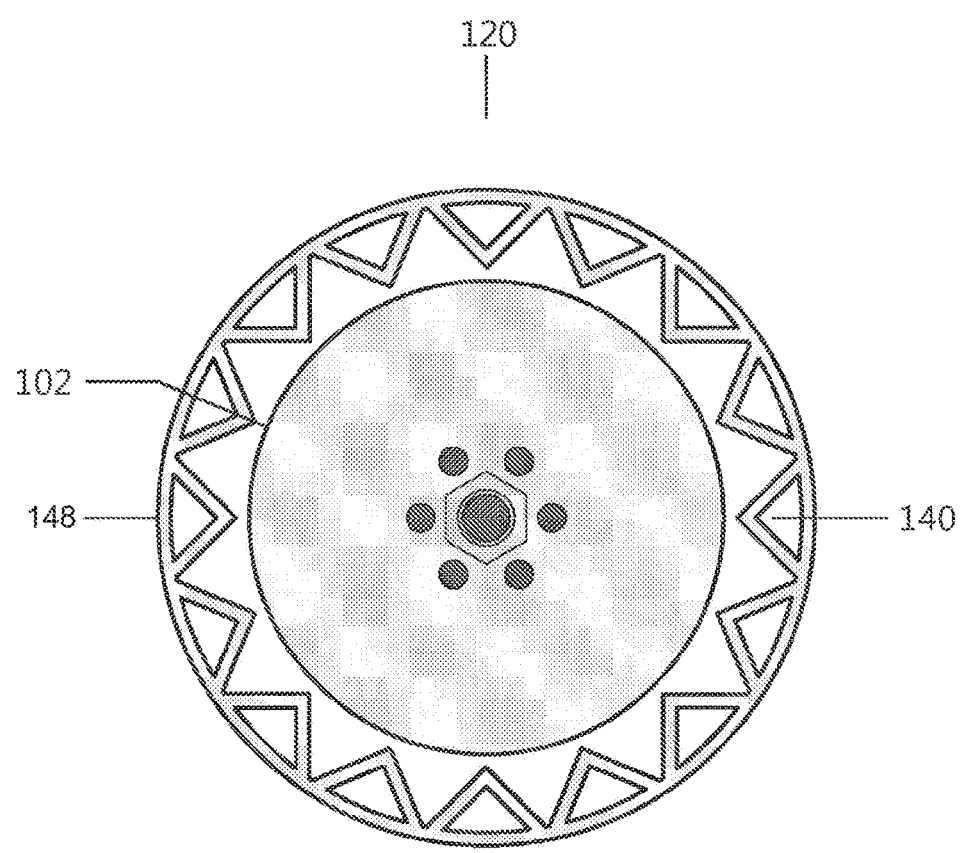
Figure 11:
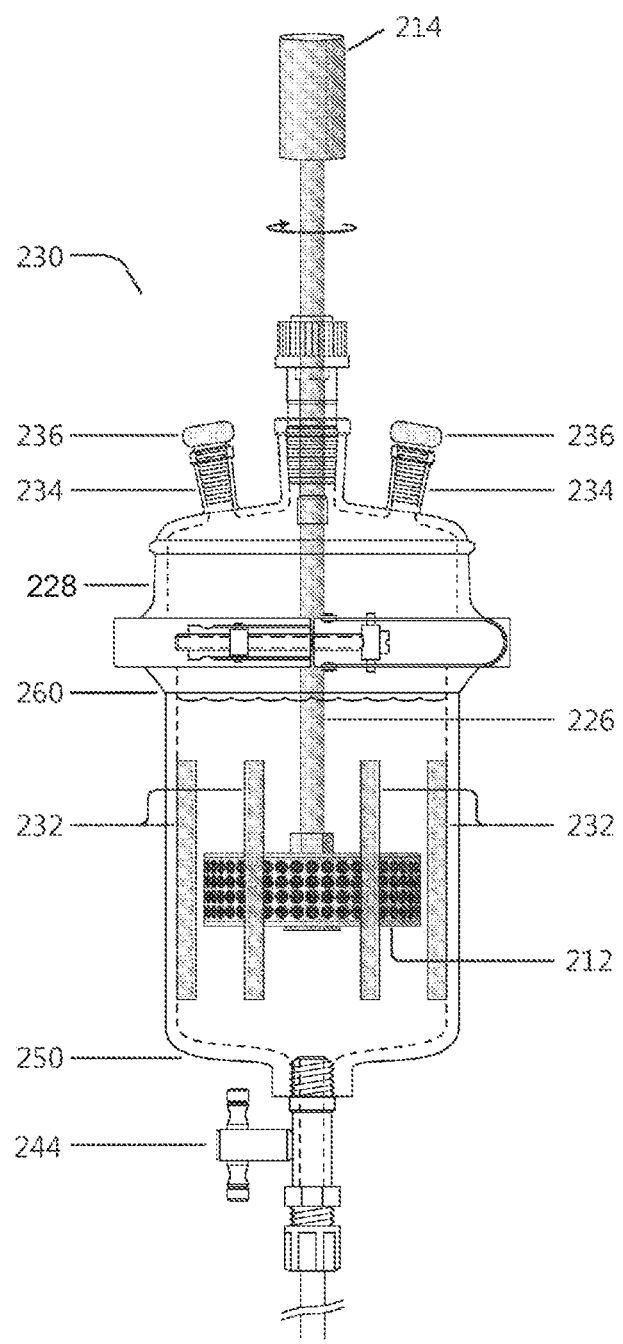
Figure 12:
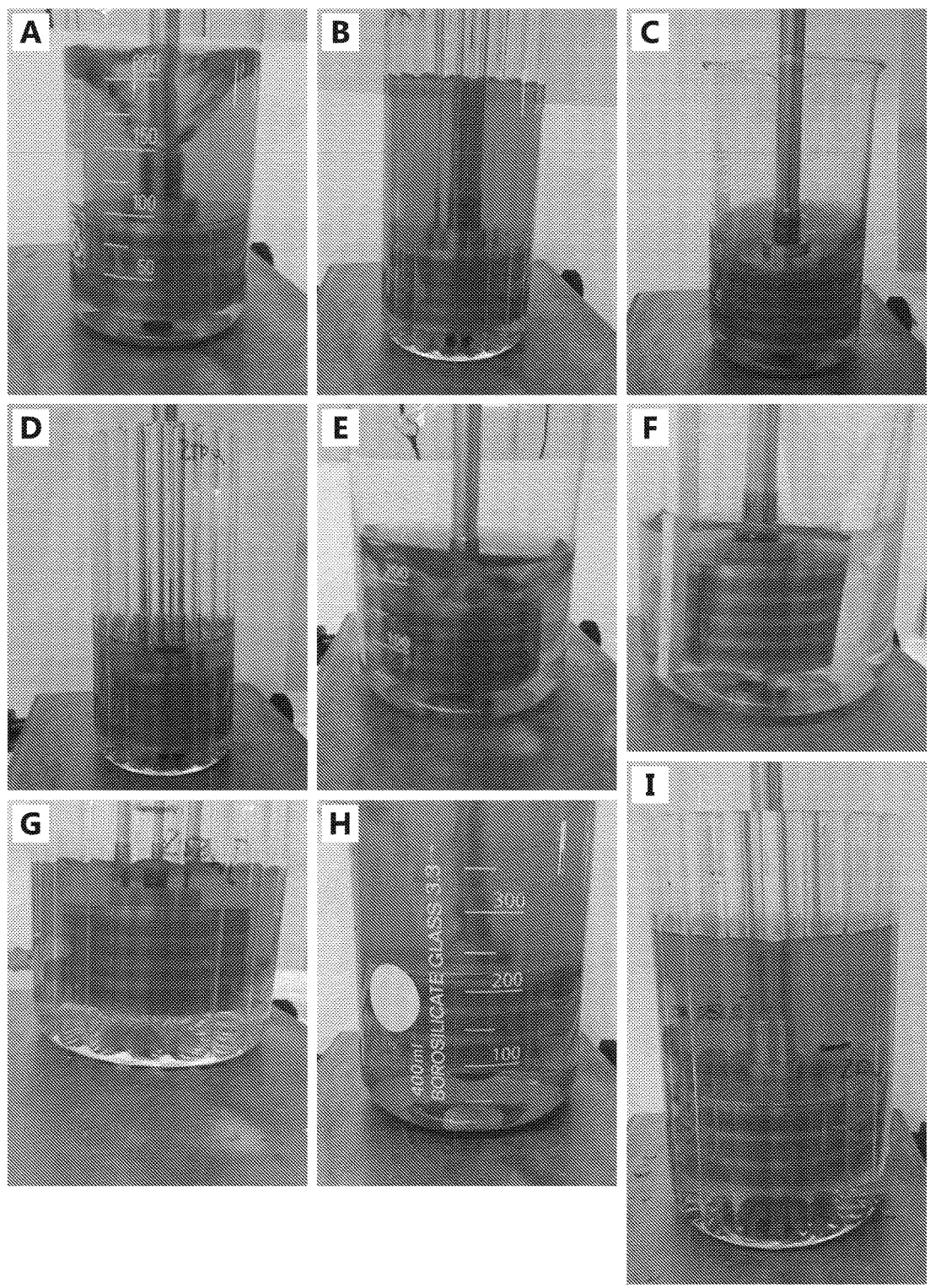

FIG. 6 presents a horizontal cross-section of a reactor comprising a transformation device and semi-elliptically-shaped grooves in the inner wall of the reactor;

FIG. 7 discloses a horizontal cross-section of a reactor comprising a transformation device and tubes on the inner wall of the reactor;

FIG. 8 describes a horizontal cross-section of a reactor comprising a transformation device and rectangular channels on the inner wall of the reactor;

FIG. 9 describes a horizontal cross-section of a reactor comprising a transformation device and semi-elliptical channels on the inner wall of the reactor;

FIG. 10 outlines a horizontal cross-section of a reactor comprising a transformation device and triangular channels on the inner wall of the reactor;

FIG. 11 shows a side view of a reactor comprising a transformation device as well as means for enhancing the fluidic shear stress in any of the two directions along said inner wall between said first end part and said second end part; and FIG. 12 presents photos showing the experimental set-ups of the experimental part of this application.

DETAILED DESCRIPTION OF PREFERRED EMBODIMENTS

Accordingly, in a first aspect the invention provides a reactor for performing, by means of at least one solid reaction member(s), a biological or chemical transformation, or physical or chemical trapping from, or release of agents to, a fluidic media, said reactor comprising a cylindrical reactor vessel having a first end part, a second end part and an inner wall between these parts, in which reactor vessel a transformation device has been mounted, said transformation device comprising a flow distributor having an essentially cylindrical shape, a first essentially flat surface, a second essentially flat surface, and a peripheral wall having an essentially circular cross-section, at least one fluid medium inlet adapted for receiving fluid medium and optionally adapted for receiving initially suspended solid reaction member(s)s located in vicinity of the centre of said first and/or second surface, at least one fluid medium outlet permeable for said fluid medium but impermeable for said solid reaction members, said outlet being located on said peripheral wall, a driving shaft located on said first surface for enabling rotation or oscillation of the flow distributor, and at least one confinement wherein said solid reaction members can be trapped and said transformation is performed; and a means for rotating and/or oscillating the device;

wherein said inner wall of the reactor vessel comprises means for enhancing the fluidic shear stress in any of the two rotary directions along said inner wall between said first end part and said second end part.

Transformation devices comprising a flow distributor and a means for rotating and/or oscillating the device have been described in WO 2011/098570.

As disclosed herein, the term "means for enhancing the fluidic shear stress" relates to some different types of structures capable of causing perturbations in the fluidic media flow close to the inner wall of the reactor vessel that is caused by the rotational movement of the flow distributor. Such means typically has a small volume, and the total volume of such means in a reactor according to the invention typically amounts to less than 10% of the total volume of the reactor vessel. In some embodiments, the total volume of such means amounts to less than 8%, 6%, 5%, 4%, 3% or 2%, respectively, of the total volume of the reactor vessel. Examples of semi-elliptically shaped grooves are given in FIG. 6, and examples of hemicylindrical, cylindrical, rectangular, and triangular shapes are given in FIGS. 7, 8, 9 and 10, but the invention is not limited to these specifically exemplified embodiments; instead numerous other shapes are conceivable, with or without hollow channels, and in varying number and height, that would cause sufficient perturbation of the shear layer to induce a turbulent flow will fulfill the criteria of a working device according to the invention and a skilled worker should be able to figure out alternative perturbating geometries falling within the scope of the invention, based on the examples given in these disclosures.

In a preferred embodiment, said means for enhancing the fluidic shear stress is at least one semi-elliptically-shaped groove in said inner wall extending in a direction from said first end part to said second end part. In one embodiment, the inner wall of the reactor vessel comprises a plurality of such semi-elliptically-shaped grooves. In one embodiment, said grooves are arranged adjacent to each other. In one embodiment, the depth of said grooves amount to 10-50% of the width of the grooves.

In a preferred embodiment, said means for enhancing the fluidic shear stress is at least one hollow structure in said wall, said hollow structure extending in a direction from said first end part to said second end part, said hollow structure having open ends above and below said flow distributor and a through-going channel there between, thereby facilitating communication between the fluidic medium above and below the flow distributor.

In a preferred embodiment, the channel has a triangular, elliptical or semi-elliptical cross-section. The cross-section of the internal channel of the hollow structure is sufficiently large in order to allow flow of fluidic medium therein. In one embodiment, the inner cross-section of the hollow structure has an internal area of at least 0.25 cm$^2$.

In a preferred embodiment, the reactor comprises 2-30 of said means for enhancing the fluidic shear stress. In other embodiments, the reactor comprises 3-30, 4-30, 5-30, 6-30 or 8-25 of said means.

In a second aspect, the invention provides a kit for performing, by means of a solid reaction member, a biological or chemical transformation, or physical or chemical trapping from, or release of agents to, a fluidic media, comprising:

a) a cylindrical reactor vessel having a first end part, a second end part and an inner wall between these parts, wherein said inner wall comprises means for enhancing the fluidic shear stress in any of the two rotary directions along said inner wall between said first end part and said second end part; and b) a flow distributor having an essentially cylindrical shape, a first essentially flat surface, a second essentially flat surface, and a peripheral wall having an essentially circular cross-section, at least one fluid medium inlet adapted for receiving fluid medium and optionally adapted for receiving suspended solid reaction member(s) located in vicinity of the centre of said first and/or second surface, at least one fluid medium outlet permeable for said fluid medium but impermeable for solid reaction member(s), said outlet being located on said peripheral wall, a driving shaft located on said first surface for enabling rotation or oscillation of the flow distributor, and at least one confinement wherein said solid reaction member(s) can be trapped and said transformation is performed.

In one embodiment said means for enhancing the fluidic shear stress is at least one semi-elliptically-shaped groove in said inner wall extending in a direction from said first end part to said second end part.

In a further embodiment, said means for enhancing the fluidic shear stress is at least one hollow structure in said wall, said hollow structure extending in a direction from said first end part to said second end part, said hollow structure having open ends and a through-going channel therebetween, thereby facilitating communication of the fluidic medium in the upper and lower parts of the reactor vessel.

In a further embodiment, the channel has an triangular, elliptical or semi-elliptical cross-section.

In a further embodiment, the reactor comprises 2-30 of said means for enhancing the fluidic shear stress.

In a third aspect, the invention provides a method of using a reactor according to any the first aspect for performing, by means of a solid reaction member, a biological or chemical transformation, or physical or chemical trapping from, or release of agents to, a fluidic media.

Turning now to the enclosed figures, FIG. 1 presents a side view of a conventional reaction set-up 10 according to the state of the art for performing a biological or chemical transformation, or physical or chemical trapping from, or release of agents to, a fluidic media by means of a solid reaction member. The set-up 10 is comprised of a reactor vessel 12 having two inlet openings 14, with stoppers 16 fitted onto a lid 18 with closure means 20 as well as an outlet opening 22 fitted with closure means 24. The reactor vessel 12 further comprises stirring means 26 powered by an electrically, pneumatically, or hydraulically driven motor 30 via a drive shaft 28. The reactor vessel 12 also comprises several voluminous baffles 32, 34, 36 joined by two ring-shaped joining members 38, 40. Such a conventional set-up is associated with the problems discussed above in the technical background section.

FIG. 2 presents a side view of an embodiment of a transformation that is a part of the present invention. The transformation device comprises a flow distributor 102 and a rotation and/or oscillation means 116, typically an electrically, pneumatically, or hydraulically driven motor, joined to the flow distributor 102 by a drive shaft 114. The flow distributor 102 has a first surface 104, a second surface 106 and a peripheral wall 108. The flow distributor 102 has an essentially cylindrical shape and the peripheral wall 108 has an essentially circular cross-section. There are fluid medium inlets 110 on the first 104 or on the second 106 surface, or optionally on both said surfaces. There are also fluid medium outlets 112 on the peripheral wall 108. The drive shaft 114 is mounted centrally on top of the first surface 104.

FIG. 3 shows a view of the first surface 104 of the flow distributor 102. There is optionally, or compulsory if there are no fluid inlets on the second surface 106 in FIG. 4, at least one fluid medium inlet 110 on the first surface 104 in close proximity to the attachment location of the drive shaft 114, or in other words adjacent to the intended axis of rotation of the second surface 104.

FIG. 4 shows a view of the second surface 106 of the flow distributor 102. There is optionally, or compulsory if there are no fluid inlets on the first surface 104 in FIG. 3, at least one fluid medium inlet 110 at, and/or adjacent to, the intended axis of rotation of the second surface 106.

FIG. 5 discloses a cross-sectional view from the first surface of an embodiment of the flow distributor 102 shown in FIG. 2 along the radial plane from A to B. In the shown embodiment, there is a plurality of confinements 130 separated from each other by separating walls 132. The confinements 130 may be fully or partially separated from each other. In the shown embodiment, there is a central fluid medium inlet 110 which is common to all confinements. In other embodiments comprising fully separated confinements there is at least one fluid medium inlet for each confinement. As already shown in FIG. 2, there are fluid medium outlets 112 arranged in the peripheral wall 108 in such a way that there is at least one such outlet 112 from each confinement 130. In the embodiment shown in FIG. 5 there is also a peripheral retaining mesh 134 along the inner surface of the peripheral wall 108. The peripheral retaining mesh 134 is permeable for the fluid reaction medium but not for the solid reaction members. In the shown embodiment, there is also, optionally and suspended on a mesh retainer 136, an inner retaining mesh 138, which also is permeable for the fluid reaction medium but not for the solid reaction members. In situations where the solid reaction member(s) are arranged in confinements 130 of the flow distributor right from the start, such an inner retaining mesh could be included in order to prevent the solid reaction members from escaping through the fluid medium inlet 110. However, in cases were solid reaction member(s) are added to and suspended in the fluid medium, such an inner retaining mesh should not be included as the solid reaction member(s) will be effectively drawn into the flow distributor 102 by its suction force and trapped therein when rotating/oscillating the flow distributor 102.

FIG. 6 presents a horizontal cross-section of a reactor 120 comprising the flow distributor 102 of a transformation device and semi-elliptically-shaped grooves 122 in the inner wall of the reactor. The distance V-V refers to the distance between the deepest points of two opposite grooves (or valleys) and V-V to the distance between two opposite ridges. Typically, the distance R-R is 70-95% of the distance V-V. Typically, the amount of grooves is 10-25.

FIG. 7 discloses a horizontal cross-section of the flow distributor 102 of a transformation device encased in a reactor 120 comprising a set of tubes 124 adapted on the inner side of the peripheral wall 148 of the reactor 120. In a manner similar to a set of conventional baffles, these tubes 124 will cause perturbations and enhanced fluidic shear stress in relation to the flow distributor 102 rotating inside reactor 120, while additionally providing flow paths between the fluid volumes above and below the flow distributor 102 to enhance the mixing of these fluid volumes, which are otherwise effectively separated by a radial flow curtain created by fluid exiting from the peripheral outlets of flow distributor 102.

FIG. 8 discloses a horizontal cross-section of the flow distributor 102 of a transformation device encased in a reactor 120 comprising a set of hollow rectangular channels 126 adapted on the inner side of the peripheral wall 148 of the reactor 120, channels 126 of which both ends are open and which lengths extend at least along the entire height of the flow distributor 102. Similar to a set of conventional baffles, these channels 126 will cause perturbations and enhanced fluidic shear stress in relation to the flow distributor 102 rotating inside reactor 120, while additionally providing flow paths between the fluid volumes above and below the flow distributor 102 to enhance the mixing of these fluid volumes, which are otherwise effectively separated by a radial flow curtain created by fluid exiting from the peripheral outlets of flow distributor 102.

FIG. 9 describes a horizontal cross-section of the flow distributor 102 of a transformation device encased in a reactor 120 comprising a set of semi-elliptical tubes 128 forming channels on the inner side of the peripheral wall 148 of the reactor 120, channels 128 of which both ends are open and which lengths extend at least along the entire height of the flow distributor 102. Similar to a set of conventional baffles, these channels 128 will cause perturbations and enhanced fluidic shear stress in relation to the flow distributor 102 rotating inside reactor 120, while additionally providing flow paths between the fluid volumes above and below the flow distributor 102 to enhance the mixing of these fluid volumes, which are otherwise effectively separated by a radial flow curtain created by fluid exiting from the peripheral outlets of flow distributor 102.

FIG. 10 outlines a horizontal cross-section of the flow distributor 102 of a transformation device encased in a reactor 120 comprising a set of triangular channels 140 on the inner side of the peripheral wall 148 of the reactor 120, channels 140 of which both ends are open and which lengths extend at least along the entire height of the flow distributor 102. These triangular channels cause perturbations and enhanced fluidic shear stress in relation to the flow distributor 102 rotating inside reactor 120, while additionally providing flow paths between the fluid volumes above and below the flow distributor 102 to enhance the mixing of these fluid volumes, which are otherwise effectively separated by a radial flow curtain created by fluid exiting from the peripheral outlets of flow distributor 102.

FIG. 11 shows a side view of a reactor 230 according to the present invention comprising a first end part 250 and a second end part 260, and further comprising a transformation device including a flow distributor 212, an electrically, pneumatically, or hydraulically driven motor 214, a lid 228 with closure means and a drive shaft 226, inlet openings 234 with stoppers 236 as well as a multitude of means 232 for enhancing the fluidic shear stress in any of the two directions along said inner wall between said first end part and said second end part, constructed according to any of the principles illustrated in FIG. 6, 7, 8, 9, or 10. The reactor 230 also comprises an outlet means 244 which can be used to empty the fluid content of the reactor after completion of the transformation, without having to filter the solution. Interstitial fluid trapped by the solid member in the flow distributor 212 can then easily be emptied into the reactor by centrifugal force, simply by allowing the flow distributor 212 to continue its rotational movement during the emptying step.

FIG. 12 illustrates the reaction set-ups used in the experimental section and will be further described in that section.

EXPERIMENTAL SECTION

The present invention will now be further described in the following examples, which are provided for illustration purposes and are not intended to limit the scope of the present invention.

Example 1

A flow distributor of the invention, constructed essentially according to FIGS. 2, 3, 4, and 5, with outer diameter 45 mm and height 30 mm, was used in the experiment, in combination with an electric overhead stirred with electronically controlled rotational speed. A standard 250 mL glass beaker of 60 mm inner diameter was used as reactor vessel, without the use of any means of baffling to reduce the solid body rotation and vortex formation. The vessel was filled with 150 ml of water into which the flow distributor was placed, pre-filled with 27 ml of water-washed active carbon (12/40 mesh) in the space between the with the optional inner retaining mesh and the peripheral retaining mesh. At this stage 0.435 ml of a 1% (w/v) solution of disodium 6-hydroxy-5-((2-methoxy-5-methyl-4-sulfophenyl)azo)-2-naphthalenesulfonate, a red foodstuff dye also known as Allura Red, C.I. 16035, FD&C Red 40, and E129, was added to the water. The flow distributor was immediately thereafter set to rotate at 500 RPM, and a decolorization experiment was continued until the solution was completely colorless. Evident from the photo in FIG. 12A, there was a strong solid body rotation accompanied by formation of a well developed vortex and the time required for complete decolorization of the solution was 510 seconds.

Example 2

The same set-up and water volume as in Example 1 was used, with the difference that the conventional beaker was substituted for a reactor vessel of the invention (60 mm outer diameter) with 18 radial undulations as in FIG. 6, with ridge-ridge (R-R) diameter 49.5 mm and valley-valley (V-V) diameter 54.3 mm, according to notations shown in said Figure. Evident from the photo in FIG. 12B, essentially no solid body rotation was seen and an accompanying vortex was thus not formed. The time required for complete decolorization was 360 seconds at a rotational rate of 500 RPM, verifying a substantial increase in mass transfer compared to Example 1.

Example 3

The same set-up as in Example 1 was used, with the difference that only 60 ml water was used in combination with the flow distributor of the invention and the unbaffled beaker. Evident from the photo in FIG. 12C, there was a strong solid body rotation accompanied by the formation of a well developed vortex extending essentially across the entire upper surface of the flow distributor. The time required for complete decolorization of the solution was 225 seconds at a rotational rate of 500 RPM.

Example 4

The same set-up and water volume as in Example 3 was used, with the difference that the flow distributor and reactor vessel of the invention were used in combination. Evident from the photo in FIG. 12D, only very limited solid body rotation was observed and hardly any vortex was formed. The time required for complete decolorized of the solution was 195 seconds at a rotational rate of 500 RPM. The reactor vessel of the invention accomplished an practically total prevention of vortex formation and a slight increase in mass transfer compared to Example 3.

Example 5

The same set-up as in Example 1 was used, with the difference that the flow distributor of the invention was used in combination with an unbaffled 400 mL beaker with inner diameter 77 mm. Evident from the photo in FIG. 12E, a strong vortex was formed that extended down to the upper inlets of the flow distributor, with unwanted suction of air as a result. The time required for complete decolorization was 600 seconds at a rotational rate of 500 RPM.

Example 6

The same set-up as in Example 5 was used, with the difference that the a 400 mL beaker (80 mm outer diameter) was now equipped with three conventional baffles made from poly(tetrafluoroethene), according to prior art. Evident from the photo in FIG. 12F, no vortex was formed and the slanted level of the water surface shows the action of the conventional baffles lead to pressure build-up between the baffles. The time required for complete decolorization was 420 seconds at a rotational rate of 500 RPM, which verifies that the conventional baffles led to increased mass transfer compared to the unbaffled beaker.

Example 7

The same set-up as in Example 5 was used, with the difference that the beaker was substituted for a reactor vessel of the invention (80 mm outer diameter) with 18 radial undulations as in FIG. 6, with ridge-ridge (R-R) diameter 69.6 mm and valley-valley (V-V) diameter 74.3 mm, according to notations shown in said Figure. Evident from the photo in FIG. 12G, no tendency of solid body rotation accompanied by vortex formation was seen. The time required for complete decolorization was 270 seconds at a rotational rate of 500 RPM, which is evident of a substantial increase in mass transfer, compared to the conventional baffles used in Experiment 6.

Example 8

The same set-up as in Example 5 was used, with the difference that the flow distributor according to the invention was now larger, with diameter was 65 mm and height 30 mm, and the water volume was increased to 300 mL to which 0.645 ml of 1% (w/v) Allura Red was added. Evident from the photo in FIG. 12H, a strong vortex was formed that extended down to the upper inlets of the flow distributor, with unwanted suction of air as a result. The time required for complete decolorization was 450 seconds at a rotational rate of 500 RPM.

Example 9

The same set-up as in Example 8 was used, with the difference that the beaker was substituted for a reactor vessel of the invention (80 mm outer diameter) with 18 radial undulations as in FIG. 6, with ridge-ridge (R-R) diameter 69.6 mm and valley-valley (V-V) diameter 74.3 mm, according to notations shown in said Figure. Evident from the photo in FIG. 12I, no tendency of solid body rotation accompanied by vortex formation was seen. The time required for complete decolorization was 375 seconds at a rotational rate of 500 RPM, which is reveals a substantial increase in mass transfer.

The person skilled in the art realizes that the present invention by no means is limited to the preferred embodiments described above. On the contrary, many modifications and variations are possible within the scope of the appended claims.

Additionally, variations to the disclosed embodiments can be understood and effected by the skilled person in practicing the claimed invention, from a study of the figures, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combinations of these measures cannot be used to advantage.

The invention claimed is:

1. A reactor for performing, by means of at least one solid reaction member(s), a biological or chemical transformation, or physical or chemical trapping from, or release of agents to, a fluidic media, said reactor comprising a cylindrical reactor vessel having a first end part, a second end part, and an inner wall between these parts, in which reactor vessel a transformation device has been mounted, said transformation device comprising
 a flow distributor having an essentially cylindrical shape, a first essentially flat surface, a second essentially flat surface, and a peripheral wall having an essentially circular cross-section, at least one fluid medium inlet located in vicinity of the centre of said first and/or second surface, said at least one fluid medium inlet being adapted for receiving fluid medium and optionally being adapted for receiving initially suspended solid reaction member(s), at least one fluid medium outlet permeable for said fluid medium but impermeable for solid reaction member(s), said outlet(s) being located on said peripheral wall, a driving shaft located on said first surface for enabling rotation or oscillation of the flow distributor, and at least one confinement wherein said solid reaction member(s) can be trapped and said transformation is performed; and
 a means for rotating and/or oscillating the device; wherein said inner wall of the reactor vessel comprises means for enhancing the fluidic shear stress in any of the two rotary directions along said inner wall between said first end part and said second end part,
 wherein said means for enhancing the fluidic shear stress is at least one hollow structure in said wall, said hollow structure(s) extending in a direction from said first end part to said second end part, said hollow structure(s) having open ends above and below said flow distributor and a through-going channel there between, thereby facilitating communication between the fluidic medium above and below the flow distributor.

2. A reactor according to claim 1, wherein said means for enhancing the fluidic shear stress is at least one semi-elliptically-shaped groove in said inner wall extending in a direction from said first end part to said second end part.

3. A reactor according to claim 1, wherein the channel has a rectangular, triangular, elliptical, or semi-elliptical cross-section.

4. A reactor according to claim 1, wherein the reactor comprises 2-30 of said means for enhancing the fluidic shear stress.

5. A kit for performing, by means of at least one solid reaction member(s), a biological or chemical transformation, or physical or chemical trapping from, or release of agents to, a fluidic media, comprising:
 a) a cylindrical reactor vessel having a first end part, a second end part and an inner wall between these parts, wherein said inner wall comprises means for enhancing the fluidic shear stress in any of the two rotary directions along said inner wall between said first end part and said second end part; and
 b) a flow distributor having an essentially cylindrical shape, a first essentially flat surface, a second essentially flat surface, and a peripheral wall having an essentially circular cross-section, at least one fluid medium inlet being adapted for receiving fluid medium and optionally being adapted for receiving initially suspended solid reaction member(s), which at least one fluid medium inlet is located at the centre of said first and/or second surface, at least one fluid medium outlet permeable for said fluid medium but impermeable for solid reaction member(s), said outlet(s) being located on said peripheral wall, a driving shaft located on said first surface for enabling rotation or oscillation of the flow distributor, and at least one confinement wherein said solid reaction member(s) can be trapped and said transformation is performed, wherein said means for enhancing the fluidic shear stress is at least one hollow structure in said wall, said hollow structure extending in a direction from said first end part to said second end part, said hollow structure having open ends and a through-going channel there between, thereby facilitating communication of the fluidic medium in the upper and lower parts of the reactor vessel.

6. A kit according to claim 5, wherein said means for enhancing the fluidic shear stress is at least one semi-elliptically-shaped groove in said inner wall extending in a direction from said first end part to said second end part.

7. A kit according to claim 5, wherein the channel has a rectangular, triangular, elliptical or semi-elliptical cross-section.

8. A kit according to claim 5, wherein the reactor comprises 2-30 of said means for enhancing the fluidic shear stress.

9. A method of using a reactor according to claim 1, the method comprising:
 performing, by at least one solid reaction member(s), a biological or chemical transformation, or physical or chemical trapping from, or release of agents to, in a fluidic media.

* * * * *